United States Patent [19]

Herbstman

[11] 4,118,425
[45] Oct. 3, 1978

[54] METHOD FOR PREPARATION OF ETHERS

[75] Inventor: Sheldon Herbstman, Spring Valley, N.Y.

[73] Assignee: Texaco Inc., New York, N.Y.

[21] Appl. No.: 792,285

[22] Filed: Apr. 29, 1977

Related U.S. Application Data

[63] Continuation of Ser. No. 584,323, Jun. 6, 1975, abandoned.

[51] Int. Cl.² ............... C07C 41/06; C07C 41/10
[52] U.S. Cl. ................ 260/614 A; 260/615 R; 260/611 A
[58] Field of Search ............. 260/614 A, 615 R

[56] References Cited

U.S. PATENT DOCUMENTS

| | | | |
|---|---|---|---|
| 2,480,940 | 9/1949 | Leum et al. | 260/614 A |
| 3,119,766 | 1/1964 | Voltz et al. | 260/614 A |
| 3,170,000 | 2/1965 | Verdol | 260/614 A X |
| 3,689,434 | 9/1972 | Suggitt et al. | 260/683.75 |
| 3,711,569 | 1/1973 | Tshopp et al. | 260/683.3 |
| 3,726,942 | 4/1973 | Louder | 260/614 A UX |
| 3,816,294 | 6/1974 | Wilson et al. | 260/683.43 |
| 3,849,082 | 11/1974 | Kozlowski et al. | 44/56 |
| 3,912,463 | 10/1975 | Kozlowski et al. | 260/614 A |

Primary Examiner—Howard T. Mars
Attorney, Agent, or Firm—Thomas H. Whaley; Carl G. Ries; Carl G. Seutter

[57] ABSTRACT

Ethers, such as the methyl ether of tertiary butanol, may be typically prepared by reacting methanol and isobutene in the presence of hydrocarbon, extracting excess methanol with water, and recovering the desired ether in hydrocarbon solution for further disposition.

9 Claims, 1 Drawing Figure

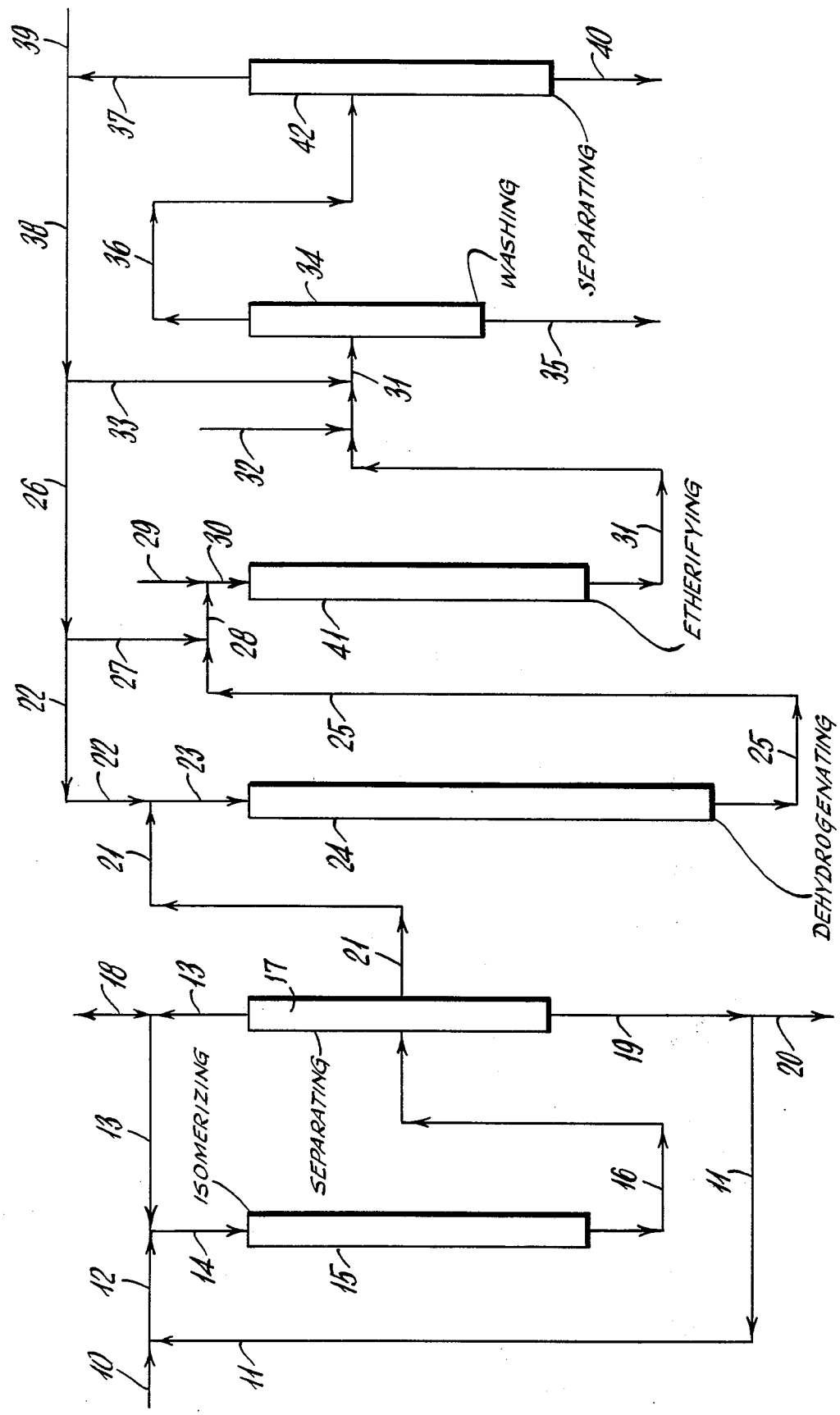

METHOD FOR PREPARATION OF ETHERS

This is a continuation of application Ser. No. 584,323, filed June 6, 1975, and now abandoned.

FIELD OF THE INVENTION

This invention relates to the preparation of ethers. More particularly it relates to the preparation of unsymmetrical ethers in high yield and purity.

BACKGROUND OF THE INVENTION

As is well known to those skilled in the art, ethers, including unsymmetrical ethers, may be prepared by reacting an alcohol with another alcohol to form the desired product. The reaction mixture, containing catalyst and/or condensing agent, may be separated and further treated to permit attainment of desired product. Such further treatment commonly includes one or more distillation operations.

It is an object of this invention to provide a process for preparing ethers. Other objects will be apparent to those skilled in the art from the following description.

SUMMARY OF THE INVENTION

In accordance with certain of its aspects, the method of this invention for preparing an ether from a hydrocarbon charge containing normal butane may comprise
  a. isomerizing said alkane hydrocarbon charge at isomerizing conditions;
  b. withdrawing from said isomerization an isomate containing isobutane and n-butane in weight ratio of 1.0-2.0:1
  c. dehydrogenating said isomate thereby forming a dehydrogenate containing isobutene and n-butane in weight ratio of 1-3:1;
  d. reacting said dehydrogenate with water-soluble alcohol in the presence of etherification catalyst at etherification reaction conditions thereby forming reaction mixture containing product ether, water-soluble alcohol, and n-butane;
  e. contacting said reaction mixture with water thereby forming (i) aqueous extract containing water-soluble alcohol and (ii) raffinate containing said normal butane and said product ether substantially free of said water soluble-alcohol; and
  f. recovering said raffinate from said contacting operation.

DESCRIPTION OF THE INVENTION

As is well known to those skilled in the art, during petroleum refining, a portion of the crude oil may be separated from or converted to lower alkanes during normal processing. Of these, hydrogen and methane may find ready use as eg components of SNG. Ethane and propane may find similar use to a limited degree; but economic considerations frequently dictate their conversion to ehtylene. Similarly $C_6$ and heavier alkanes may find use as components in gasoline fractions.

Accordingly the refiner may be presented with hydrocarbon streams containing 4 or 4-5 carbon atoms. It may be desirable to use such a stream as a charge to alkylation or alternatively as a petrochemical charge stream. A desirable possible use of such a stream, after preliminary treating is found to be the preparation of ethers.

Typically such a charge stream may be a normal alkane stream containing less than 2% w of other hydrocarbons. In a typical operation, the charge stream may be substantially pure (i.e. greater than 98% w) normal alkanes. The charge stream may contain for example 30% w-100% w, say 50% w of normal butane and 0%-70%, commonly 30% w-70% w, say 50% w of normal pentane.

A typical commonly available charge contains 56% w normal butane and 44% w normal pentane. In one preferred embodiment it may contain substantially pure normal butane.

In practice of the process of this invention there is passed to an isomerizing operation an isomerization charge stream containing the above-noted charge — frequently plus recycle normal pentane (as hereinafter noted when it is desired to produce a preferred mixture of t-butyl and t-amyl ethers) to form an isomerization charge containing 10-30 parts, say 19 parts of normal butane and 0-15, more typically 5-15 parts, say 11 parts of normal pentane.

It is a feature of the process of this invention according to one preferred embodiment that during isomerization, normal butane is converted to isobutane in amount to give a product isomate containing desired proportions of normal butane and isobutane whereby the n-butane (as hereinafter noted) is the prescribed quantity for the etherification and washing operations while the isobutane (after dehydrogenation to isobutene) is the prescribed coordinated quantity for the etherification operation.

In particular the weight ratio of normal butane to normal pentane admitted to isomerization is controlled in a preferred embodiment (as by selection of alkane charge and/or recycle of normal pentane) to be within the ratio of 1.5-2.0:1, say about 1.7:1. If the ratio be substantially below 1.5:1, then it may be found that the isomerization occurs to yield isobutane in amount which is less than is preferred (to give ultimate yield of methyl t-butyl ether) and to yield un-isomerized n-butane which is more than is preferred (to be present during etherification and/or washing).

If the ratio be substantially above 2.0:1, then it may be found that the isomerization may occur to yield isobutane in amount which is greater than is preferred and un-isomerized n-butane in amount which is less than is preferred.

It will be apparent that the various streams may contain various amounts of other components typified by diolefins such as butadiene or isopentadiene (particularly after eg dehydrogenation); but these may be essentially inert and may be removed from the stystem in a separation operation if desired.

Isomerization of the isomerization charge is typically carried out in the presence of activated alumina such as that prepared by the process disclosed in U.S. Pat. No. 3,689,434 or U.S. Pat. No. 3,607,959 or U.S. Pat. No. 3,523,142 or U.S. Pat. No. 3,816,294.

The catalyst typified by those off U.S. Pat. No. 3,689,434 may be prepared by contacting alumina with an activator system comprising (a) chlorine or bromine and (b) an inorganic sulfur compound which may be hydrogen sulfide or $S_m X_2$ (wherein $m$ is 1-2 and X is chlorine or bromine) or alternatively $C_2Cl_4$. Activation is typically effected at 350° F. -750° F., say 575° F., at pressure of 0-500 psig, say 50 psig, for 10-30 hours, say 20 hours. The mole ratio of chlorine or bromine to inorganic sulfur may be 0.1-4:1 or alternatively the mole ratio of chlorine to $C_2Cl_4$ may be 1:1-2:1, say 1.2:1.

Preferably the catalyst also contains 0.01-5% w of platinum, palladium, rhodium, or ruthenium. A preferred isomerization catalyst may be that prepared by the process of Experimental Example I of U.S. Pat. No. 3,689,434 — a chlorided platinum on alumina catalyst.

Isomerization of the charge stream containing paraffinic components in practice of the process of this invention may be effected by passing 100 parts by weight (this number serving as a basis for the numbers that follow) in liquid phase (except for the hydrogen which is in the gas phase) at 300°-400° F., preferably 310° F. -375° F., say 335° F. and pressure of 100-1000 psig, preferably 300-700 psig, say 300 psig to an isomerization operation.

There is also passed to said isomerizing operation, hydrogen in amount of 0.1-5, preferably 0.2-3.0, say 1.5 moles per mole of hydrocarbon charge. This may correspond to a hydrogen rate of 300-15,000, preferably 600-10,000, say 5,000 SCFB. The hydrogen purity may be 50-100 percent, preferably 80-100 percent, say 95 percent by volume. The space velocity (LHSV) of the total charge through the catalyst bed may be 0.5-8, preferably 1-3, say 2.

It is a feature of the process of this invention that isomerization be controlled (by varying the time in contact with the catalyst or the space velocity VHSV). In this connection it should be noted that the space velocity is determined in terms of weight of flowing liquid and empty reaction vessel volume.

Effluent isomate from isomerization typically includes (ex hydrogen) the following:

TABLE

| Component | Parts | Typical |
| --- | --- | --- |
| normal butane | 10-30 | 19 |
| isobutane | 10-50 | 31 |
| normal pentane | 5-15 | 10 |
| isopentane | 20-60 | 40 |

The isomerization operation is typically controlled to yield isomate (ex hydrogen) wherein the product stream is characterized by a weight ratio of isobutane to normal butane of 1.0-2.0:1, preferably 1.2-1.8:1 say 1.7:1, and by a weight ratio of isobutane to isopentane of 0.5-1:1 preferably 0.6-0.8:1, say 0.77:1. The first of these ratios is determined by the conversion of normal butane to isobutane which is a function of temperature, space velocity, pressure, catalyst activity etc. In the preferred embodiment, these are controlled within the above ranges so that the conversion of normal butane is 50-100%, typically 95% of that attained at equilibrium. By way of illustration, at 335° F. and 2 LHSV with the other conditions as preferred above, the conversion of charge n-butane is 50%-62%. Equilibrium conversion is about 62%. Thus in this illustrative statement the conversion is 80%-100% of that attained at equilibrium.

Isomate so prepared is passed to a separation operation wherein (in one or more flash drums and/or distillation towers) there may be recovered 10-20 parts, preferably 12-17 parts, say 15 parts of hydrogen which is recycled to isomerization. When the charge to isomerization contains both $C_4$ and $C_5$ hydrocarbon, there is also recovered 7-15 parts, preferably 9-12 parts, say 10 parts of a stream identified as a normal pentane stream — which may be recycled to isomerization. This normal pentane stream may contain 0-2 parts, preferably 0-1 parts, say 0 parts of isopentane.

Because of the separation of the normal pentane from the isomate, the stream is referred to as depentanized isomate; and it typically contains 15-25 parts, say 19 parts of normal butane, 20-40 parts, say 31 parts of isobutane, and 30-50 parts, say 40 parts of isopentane.

It will be apparent that when the charge stream to isomerization consists essentially of a $C_4$ stream i.e. butanes, the isomate stream may contain little or no $C_5$'s. In this embodiment, separation may normally include steps which recover hydrogen and optionally steps to remove any undesirable components of isomate or to more finely balance the content of eg n-butane and isobutane.

It is a feature of the process of this invention that this stream which is to be passed to dehydrogenation be substantially free of normal pentane i.e. that it contain less than about 1 wt% of normal pentane. Typically it will contain 0-1 wt% normal pentane; and preferably it will be substantially free of normal pentane.

Optionally there may be added to the depentanized isomate a recycle stream from a separation operation; and this recycle stream may contain 10-30 parts, say 19 parts of normal butane. Total charge to dehydrogenation may thus include the following:

TABLE

| Component | Parts | Typical |
| --- | --- | --- |
| normal butane | 20-50 | 38 |
| isopentane | 60-100 | 80 |
| isobutane | 40-80 | 62 |

The so-formed depentanized isomate is dehydrogenated. Typically this is carried out over 15-25%, say 19% chromium-on-alumina catalyst (qv U.S. Pat. No. 3,711,569) at 900°-1100° F., say 1060° F. and 0-1000 psig, say 15 psig and VHSV of 200-400, say 350 to give a conversion of isobutane to isobutene of typically 60%, ispentane to isopentenes of typically 70%, and normal butane to butenes of about 50%.

Dehydrogenate typically contains:

TABLE

| Components | Parts | Typical |
| --- | --- | --- |
| normal butane | 10-30 | 19 |
| butenes | 10-30 | 19 |
| isobutane | 20-30 | 25 |
| isobutylene | 25-45 | 37 |
| isopentane | 15-25 | 22.5 |
| isopentenes | 45-65 | 57.5 |

The dehydrogenate is particularly characterized by its content of (i) isoalkenes i.e. isobutene and isopentene and (ii) normal butane. Specifically in the preferred embodiment the conent of isobutene and isopentene(s) is controlled (by isomerization, separation, and dehydrogenation) to yield a weight ratio of isobutene to isopentenes of 0.4-0.8:1, say 0.6:1, — as this yields the preferred ultimate ratio of t-butyl to t-amyl ethers.

The dehydrogenate is also characterized by a balanced content of n-butane-typically 10-30% w, say 19% w (of total hydrocarbon) which is suitable for etherification and washing as hereinafter noted. This is equivalent to a weight ratio (of isobutene-to-n-butane of 1-3:1, preferably 1.5-5:1, say 2:1.

It is a particular feature of the process of this invention that the dehydrogenate (preferably as produced or at least as diluted by recycle or addition from outside sources) is characterized by substantial absence of normal pentane. Although this stream may contain 0-1% w, say up to 1% w normal pentane, it is preferred that it be substantially free of normal pentane.

In the event that the needs of the system dictate production of eg pure eg methyl t-butyl ether, a separation may be employed to remove undesired iso-$C_5$ after or before dehydrogenation; and in the event the desired product were pure eg methyl t-amyl ether, a separation may be employed to remove undesired eg iso-$C_4$ before or after dehydrogenation.

The dehydrogenate is passed to etherification wherein the isobutylene and the isoamylenes are reacted with a water-soluble alcohol, which may be a monohydroxy alcohol or a polyhydroxy alcohol. When it is a monohydroxy alcohol it may be:

TABLE

| methanol |
| --- |
| ethanol |
| n-propanol |
| i-propanol |
| n-butanol |
| i-butanol |
| s-butanol |
| t-butanol |
| benzyl alcohol, etc. |

When the water-soluble alcohol is a polyhydroxy alcohol, it may be:

TABLE

| ethylene glycol |
| --- |
| propylene glycol |
| pentaerythritol |
| glycerol |
| trimethylol propane |
| sorbitol etc. |

In the preferred embodiment, the preferred water-soluble alcohol is an aliphatic alcohol having 1-6 carbon atoms, and more preferably a monohydroxy alcohol. The more preferred alcohols may be monohydroxy aliphatic alcohol containing less than 4 carbon atoms. The most preferred alcohol may be methanol.

Etherification may be carried out using the following reaction conditions:

TABLE

| Conditions | Broad Range | Preferred Range | Preferred Value |
| --- | --- | --- | --- |
| Temperature ° F. | 100-300 | 150-250 | 200 |
| Pressure psig | 50-750 | 50-500 | 300 |
| Isoalkene (parts) | 5-50 | 15-40 | 25 |
| Alcohol (parts) | 20-90 | 15-40 | 25 |
| Inert hydrocarbons (parts) | 5-100 | 40-90 | 50 |

It is a particular feature of the process of this invention that the mole ratio of the isoalkene to the alcohol may be at least about 0.8. It will be found however that the advantages inherent in the process may be attained to a greater degree if this ratio is greater than 1 and preferably 1.2-4.0, say 2.0. Presence of the excess of e.g. methanol facilitates purification of the desired unsymmetrical ethers and increases the life and selectivity of the catalysts used for preparation.

Etherification may be preferably carried out in the presence of a solid resin etherification catalyst. These catalysts are preferably relatively high molecular weight carbonaceous materials containing at least one —$SO_3H$ group as the functional group. Typical of these catalysts are the sulfonated coals ("Zeo-Karb H," "Nalcite X" and "Nalcite AX") produced by the treatment of bituminous coals with sulfuric acid. These materials are usually available in a neutralized form and in this case must be activated to the hydrogen form by treatment with a strong mineral acid such as hydrochloric acid, followed by water washing to remove sodium and chloride ions prior to use.

The sulfonated resin type catalysts are preferred for use in the present invention. These catalysts include the reaction products of phenol-formaldehyde resins and sulfuric acid ("Amberlite IR-1", "Amberlite IR-100", and "Naleite MX"). Also useful are the sulfonated resinous polymers of coumarone-indene with cyclopentadiene; sulfonated polymers of coumarone-indene with furfural; sulfonated polymers of coumarone-indene with cyclopentadie and furfural; and sulfonated polymers of cyclopentadiene with furfural.

The most preferred cationic exchange resins are strongly acidic exchange resins consisting essentially of sulfonated polystyrene resin, for instance, a divinylbenze cross-linked polystyrene matrix having 0.5-20% and preferably 4-16% of copolymerized divinylbenzene therein. bearing ionizable or functional nuclear sulfonic acid groups. These resins are manufactured and sold commercially under various trade names such as "Dowex 50", "Nalcite HCR" and "Amberlyst 15". As commercially obtained they have a solvent content of about 50% and can be used as is or the solvent can be removed first. The resin particle size may typically be 10 to 50 mesh (United States Sieve Series).

The reaction may be carried out in either a stirred slurry reactor or in a fixed bed continous flow reactor. The catalyst concentration should be sufficient to provide the desired catalytic effect. Generally catalyst concentration should be 0.5-50% (dry basis) by weight of the reactor contents, preferably 1-25%.

Although some of the advantages of the process of this invention may be attained if the normal butane (in liquid phase) is present during washing as hereinafter noted, it is a particular feature of the process of this invention that there is also present during etherification the liquid normal butane which is substantially free of normal pentane. If the normal butane were replaced by the same amount of normal pentane, the etherification yield of ether is unexpectedly less than half that attained with normal butane, say 43.5% w.

The typical crude product stream exiting etherification includes:

TABLE

| Component | Parts | Typical |
| --- | --- | --- |
| Methyl t-butyl ether | 40-70 | 58 |
| Methyl t-amyl ether | 70-90 | 84.5 |
| Methanol | 40-70 | 47 |
| Normal butane | 15-25 | 19 |
| Isobutene | 0-1 | 0 |
| Isopentene(s) | 0-1 | 0 |
| Isopentane | 15-25 | 22.5 |
| Butenes | 15-25 | 19 |

Water in amount of 10-100 parts, preferably 30-75 parts, say 50 parts is added to the reaction mixture at 60°-100° F., preferably 80°-90° F., say 85° F. and intimately mixed. In typical operation, a small number of contacting steps may be employed; in the preferred embodiment, a single contacting step is employed.

During the contacting operation, there is formed 70-150 parts, preferably 90-110 parts, say 107 parts of aqueous extract containing 1-20 parts, preferably 40-70 parts, say 47 parts of water-soluble alcohol typically methanol. The raffinate may contain substantially no alcohol, 0-1 parts, say 0 parts of isobutene, 0-1 parts, say 0 parts of isopentenes, 40-70 parts say 58 parts of product methyl t-butyl ether, 70–90 parts, say 84 parts of product methyl t-amyl ether, and 15–25 par say 19 parts of normal butane 15–25 parts, say 22 parts of isopentane and 15–25, say 19 parts of butylenes.

Presence of the organic phase during the water washing keeps the product ether out of the water phase; if there were no organic phase, a substantial portion of the ether would be extracted into the aqueous phase and be lost from the system (or in the alternative require special processing including distillation to permit recovery).

The water layer separated from the washing operation typically contains 40–70 parts, say 50 parts of water and 40–70 parts, say 47 parts of water-soluble alcohol, typically methanol.

The hydrocarbon layer recovered from washing typically contains:

TABLE

| Component | Parts | Typical |
| --- | --- | --- |
| Methyl t-butyl ether | 40–70 | 58 |
| Methyl t-amyl ether | 70–90 | 84.5 |
| Normal butane | 15–25 | 19 |
| Isobutene | 0–1 | 0 |
| Isopentene(s) | 0–1 | 0 |
| Isopentanes | 15–25 | 22.5 |
| n-butylenes | 15–25 | 19 |

Separation of desired product ether mix is preferably effected by flashing or distillation to recover as overhead the normal butane, isobutene, and isopentene, and as bottoms the desired product ethers methyl t-butyl ether and methyl t-amyl ether. Overhead may be recycled in whole or in part to etherification or dehydrogenation. Product ether is recovered in yields of greater than 80%; and stoichiometric yields are frequently achieved. The ether is substantially free of undesirable components including methanol, water, etc.

It is a particular feature of the process of this invention that the treatment of a charge stream containing normal butane and optionally normal pentane may be carried out using the noted conditions of operation in isomerization, dehydrogenation, etherification, and water washing so that subsequent steps may be carried out with minimum trouble and with maximum efficiency to yield the desired product. For example, control of isomerization as indicated permits attainment in the preferred embodiment of the desired conversion of normal butene; etherification and washing steps are carried out in the presence of the desired amount of normal butane. Similarly the control of isomerization yields the preferred ratio of the isobutane to isopentane to achieve ultimately the desired ratio of the ethers, etc.

The novel product ether prepared by the process of this invention may be a pure product e.g. methyl t-butyl ether, methyl t-amyl ether, etc. In one preferred embodiment however, it is a mixture containing 40–70 parts, say 58 parts of methyl t-butyl ether and 50–90 parts, say 84 parts of methyl t-amyl ether.

This preferred mixture of product ethers permits attainment of desired product gasolines. Specifically it is found that the use of pure methyl t-butyl ether in gasoline may contribute to undesirable increase in gasoline RVP (Reid Vapor Pressure). Use of the novel combination of ethers permits attainment of increased octane numbers in gasolines without any undesirable increase in RVP. This may be particularly useful in preparation of gasolines suitable for use in summer — in which a high RVP is to be avoided.

The preferred ether mixtures of this invention may include 30–60%, say 41% w of methyl t-butyl ether and 50–70%, say 59% w of methyl t-amylether. This may correspond to a weight ratio of the butyl ether to the amylether of 0.6–0.86, preferably 0.65–0.75, say 0.69.

Preferred product gasoline compositions may include 1000–2200 parts, say 1000 parts of gasoline, 40–70 parts say 41 parts of methyl t-butyl ether, and 50–90 parts, say 59 parts, of methyl t-amylether.

It is also a feature of this invention that the novel mixture of methyl t-butyl ether and methyl t-amyl ether may be recovered as or converted into a concentrate which is particularly useful for further processing. This concentrate may contain preferably 40–70 parts, say 58 parts of methyl t-butyl ether, 70–90 parts, say 84.5 parts of methyl t-amyl ether, and 10–500 parts, preferably 50–150, say about 100 parts of inert diluent-solvent.

The diluent-solvent may be a liquid in which the mixed ethers are preferably miscible or soluble; and preferably it may be a liquid which is characterized either by (i) its ease of removal, as by distillation, from the mixed ethers or (ii) by its innocuous or inert character which permits it to be retained in the mixture when it is used in subsequent processing — as in gasoline formulation.

Typical of the first group, characterized by ease of removal may be the components present in the hydrocarbon layer recovered from washing. Other diluent-solvents which may be employed may be other liquids (having preferably much higher or somewhat lower boiling points than the butyl and amyl ethers) such as other ethers or hydrocarbons. Typical of such may be t-butyl acetate, ethyl ether, methoxy benzene etc.

The preferred diluent-solvent is a "gasoline precursor". The term "gasoline precursor" as used herein includes a component which is (i) substantially miscible with the desired product ether and with gasoline and (ii) substantially immiscible with water and (iii) not an undesirable component when mixed with a gasoline. In the preferred embodiment, the gasoline precursor may contain a substantial proportion of aromatics e.g. greater than about 30%, and it may typically contain a major portion, greater than 50% aromatic components. It may be substantially pure benzene, toluene, xylene(s), etc.

It may be a component of a gasoline (i.e. a hydrocarbon including an alkylate or a naphtha) which is to be blended with other components to form a gasoline.

It may be an alkylate, a reformate, a fluid-cracked light or heavy naphtha, a naphtha from hydrocrackate, an isomerizate, etc. In a preferred embodiment, it may be a gasoline se (leaded or unleaded).

Illustrate concentrates may be the following:

| | | |
| --- | --- | --- |
| 1. | The hydrocarbon layer recovered from washing as tabulated supra. | |
| 2. | Methyl t-butyl ether | 41 parts |
| | Methyl t-amyl ether | 59 parts |
| | Gasoline | 100 parts |
| 3. | Methyl t-butyl ether | 55 parts |
| | Methyl t-amyl ether | 70 parts |
| | Gasoline | 200 parts |
| 4. | Methyl t-butyl ether | 60 parts |
| | Methyl t-amyl ether | 80 parts |
| | Toluene | 250 parts |

Practice of the process of this invention will be apparent to those skilled in the art from the following description wherein, as elsewhere in this specification, all parts, including percentages etc. are by weight unless otherwise stated. The attached drawing represents a schematic flowsheet in which the process of this invention may be carried out. It will be apparent that the drawing is schematic and various pumps, heat exchangers, distillation towers, etc. are not specifically shown.

DESCRIPTION OF A PREFERRED EMBODIMENT

In practice of the process of this invention according to a preferred embodiment, there is admitted through line 10 a charge mixture containing 100 parts of normal butane and 79 parts of normal pentane. Normal pentane, in amount of 21 parts is admitted through line 11 to form in line 12 a mixture of 100 parts of normal butane and 100 parts of normal pentane. 20 parts of hydrogen are admitted through line 13 and the mixture is passed through line 14 to isomerization operation 15.

Isomerization operation 15 is carried out in the presence of 1/16 inch diameter aluminia (Houdry 3H) which has been activated by passing tetrachlorethane $C_2H_2Cl_4$ (in amount of 20 volumes per 100 volumes of catalyst) and chlorine (in mole ratio of $Cl_2:C_2H_2Cl_4$ of 1.2:1) in air (at a rate of 270 pounds per hour per square foot of cross-section of empty catalyst vessel) through the catalyst for 20 hours at 575° F. and 50 psig.

The activated catalyst is stabilized by passing nitrogen through the catalyst at 270 lbs/hr ft² (i) for 2 hours at 800° F. and 50 psig and then (ii) with added hydrogen chloride at 0.059 lbs/hr ft² for 7 hours at 350° F. and 0 psig.

Isomerization is controllably effected at 335° F. and 300 psig. Specifically isomerization is controlled so that the conversion is about 95-100% of the equilibrium conversion (the equilibrium conversion is 95% at temperature of 335° F.). Thus the actual conversion is 50-80% and this yields a product isomate containing 38 parts of n-butane, 62 parts of isobutane, 21 parts of n-pentane, and 79 parts of isopentane. The weight ratio of isobutane to normal butane is 1.63 and the weight ratio of isobutane to isopentane is 0.78. Hydrogen is also present in amount of 20 parts.

Isomate so prepared is passed through line 16 to separation operation 17 schematically shown wherein hydrogen is recovered and recycled through line 13 (draw-off or make-up may be added through line 18). 21 parts of normal pentane is recovered through line 19 and recycled through line 11. Make-up or more preferably draw-off of normal pentane may be through line 20.

The depentanized isomate withdrawn through line 21 contains 38 parts of normal butane, 62 parts of isobutane, 79 parts of isopentane, and 0 parts of normal pentane. It will be noted that the normal pentane is substantially absent from this stream. This stream may contain "inserts" including e.g. two parts of butadiene, two parts of isopentadiene, etc. which although undesirable do not exert any undue influence on the subsequent system.

The stream in line 21 may be optionally "enriched" by a recycle stream in line 22 containing 19 parts of normal butane, 25 parts of isopentane, and 0–1 parts of isobutene. The so combined stream is passed through line 23 to dehydrogenation operation 24.

Dehydrogenation is carried out over 18% chromia-on-alumina (prepared as in Example I of U.S. Pat. No. 3,711,569) at 1060° F. and 15 psig in vapor phase at VHSV of 350. Conversion of isobutane is 50%; conversion of isopentane is 71%.

Dehydrogenate contains 19.0 parts normal butane,
19.0 n-butenes
25.0 parts isobutene,
37.0 parts isobutene,
21.5 parts isopentane,
57.5 parts isopentenes,
0 parts normal pentane,
1 parts isopentadiene.

It will be noted that the weight ratio of isobutene to isopentenes is 0.64 and that normal butane is present in amount of 11.9% w of the total. Normal pentane is present in amount of 0% of the total.

Dehydrogenate, in total amount of 151 parts, is passed through line 25 to etherification. Optionally a portion of the stream 26 may be passed through line 27 to form a combined stream in line 28. 91 parts of anhydrous methanol are admitted through line 29; and the etherification charge is passed through line 30 to etherification operation 41.

The mole ratio of methanol to isobutene plus isopentene in line 30 is about 2. Charge in line 30 is in liquid phase. Operation 41 contains as catalyst Amberlyst 15 brand of hydrogen form of a divinylbenzene cross-linked, sulfonated polystyrene solid resin etherification catalyst.

As the reactants pass downwardly through the bed at WHSV of 2 based upon isoalkene charge, the reactor is maintained at 300 psig and 200° F. During passage through the catalyst bed, (i) the methanol and isobutene react to form methyl t-butyl ether and (ii) the methanol and isopentene react to form methyl t-amyl ether.

Conversion of isobutene and isopentene is over 97%, no olefin polymers are observed, and components such as butene-1, cis- and trans-butene-2, isobutane, n-butane, and corresponding $C_5$'s pass through etherification as inerts — i.e. they are not converted to other products during etherification. Presence of normal butane substantially permits attainment of product stream containing 53% w ethers.

Crude etherification product stream (267.0 parts in line 31 in this embodiment contain 58 parts of methyl t-butyl ether, 84.5 parts of methyl t-amyl ether, 19.0 parts of n-butane, 0 parts of n-pentane, 40.4 parts of methanol, 0 parts of isobutene, 0 parts of isopentene(s) + 19 parts. of n-butenes + 21.5 parts of isopentanes +25.0 parts of isobutane.

Water in amount of 50 parts is added at 85° F. through line 32 and mixed with the etherification reaction mixture. If desired, a recycle stream containing normal butane may be added through line 33; but this is normally not necessary.

During contacting in washing operation 34 there is formed 95.5 parts of aqueous extract containing 40.0 parts of methanol, and 50 parts of water. The amount of ethers or other components present, because of the presence of the normal butane is less than 0.1 parts (and typically 0.05 parts or less). This aqueous extract is withdrawn through line 35.

Raffinate, withdrawn through line 36 in amount of 207.5 parts, contains 57 parts of methyl t-butyl ether, 83 parts of methyl t-amyl ether, 19 parts of normal butane, 0 parts of normal pentane, 0 parts of isobutane, 0 parts of isopentene(s), 1 part of water, 0 parts of methanol, 20 parts isopentane, and 22.5 parts isobutane.

Separation of desired ether product from the parts of total raffinate in line 36 is effected by distillation in operation 42. Overhead includes 19 parts of normal butane, 0 parts of normal pentane, 0 parts of isobutene, 0 parts of isopentene, 22.5 parts isobutane, and 20.0 parts isopentane.

Overhead in total amount of 61.5 parts is withdrawn through line 37 and may be recycled through line 38 or withdrawn through line 39 depending on the needs of the system.

Desired product ether in total amount of 140 parts is recovered through line 40 — corresponding to 98% w of the stoichiometric based on isopentene(s) and isobutenes admitted to etherification. Product ether mix contains 57 parts (41% w) of methyl t-butyl ether and 83 parts (59% w) of methyl t-amyl ether.

It is a particular feature of this preferred novel blend of ethers, that it unexpectedly permits maximum improvement in properties of blended gasolines.

It is found that improvements are attained in Research Octane Number (RON) and Motor Octane Number (MON) when using a gasoline containing either the methyl t-butyl ether (MTBE) or methyl t-amyl ether (MTAE) or mixtures of e.g. 41% w of the former and 59% w of the latter. In comparative tests wherein each of MBTE, MTAE, and the mixture of both were present in a gasoline in amount of 10% volume of the gasoline, the clear octane numbers and the RVP (psi at 77° F.) are as noted in the following table:

TABLE

| Composition | RVP | RON | RON CHANGE | MON | RON CHANGE |
|---|---|---|---|---|---|
| No ether | 8.4 | 92.1 | — | 83.7 | |
| MTBE | 9.1 | 94.9 | 2.8 | 85.5 | 1.8 |
| MTAE | 8.4 | 94.2 | 2.1 | 85.3 | 1.6 |
| Mixture | 8.4 | 94.7 | 2.6 | 85.4 | 1.7 |

From the above table, the following will be noted:

1. Use of MTBE along gives an increase in RON of 2.8 units and an MON of 1.8 units — however it undesirably increases the RVP to 9.1.

2. Use of MTAE alone permits maintenance of desired RVP (of 8.4 psi) but yields a lower RON and MON than may be achieved with MTBE alone.

3. Use of the preferred mixture of MTAE and MTBE permits attainment of the following desirable and unexpected results:
  (i) attainment of RON which is greater than that attained with MTAE and about as good as that attained with MTBE alone;
  (ii) attainment of MON which is greater than that attained with MTAE and almost equal to that attained with MTBE alone; and
  (iii) attainment of product gasoline mixture unexpectedly characterized by RVP of 8.4 which is substantially equal to that of gasoline containing no ether.

It is unexpected to find that it is thus possible to achieve such increases in octane number coupled with the ability to maintain the RVP constant. This is particularly important for example in preparing gasolines to be used for summer driving — which gasolines require low RVP. The ability to prepare gasolines characterized by improved octane and constant volatility represents a desiderata which is attained to maximum advantage by the technique of this invention.

Although this invention has been illustrated by reference to specific embodiments, it will be apparent to those skilled in the art that various changes and modifications may be made which clearly fall within the scope of this invention.

I claim:

1. The method of preparing ether from an alkane hydrocarbon charge containing normal butane which comprises
  a. isomerizing said alkane hydrocarbon charge at isomerizing conditions including temperature of 300° F.–400° F. and pressure of 100–1000 psig in the presence of an isomerization catalyst and in the presence of 0.1–5 moles of added hydrogen per mole of hydrocarbon charge, wherein the space velocity (LHSV) of the total charge is 0.5–8;
  b. withdrawing from said isomerization an isomate containing isobutane and n-butane in weight ratio of 1.0–2.0:1;
  c. dehydrogenating said isomate at 900° F.–1100° F. and 0–1000 psig thereby forming a dehydrogenate containing isobutene and n-butane in weight ratio of 1–3:1;
  d. reacting said dehydrogenate with at least one water-soluble aliphatic $C_1$ to $C_6$ alcohol in the presence of etherification catalyst at etherification reaction conditions including temperature of 100° F.–300° F. and 50–750 psig thereby forming reaction mixture containing product ether, water-soluble alcohol, and n-butane;
  e. contacting said reaction mixture with water thereby forming (i) aqueous extract containing water-soluble alcohol and (ii) raffinate containing said normal butane and said product ether substantially free of said water-soluble alcohol;
  f. recovering said raffinate from said contacting operation; and
  g. recovering said product ether from said raffinate.

2. The method of preparing a mixture of a tertiary butyl ether of a $C_1$ to $C_6$ alkanol and a tertiary amyl ether of a $C_1$ to $C_6$ alkanol from an alkane hydrocarbon charge containing normal butane and normal pentane which comprises
  a. isomerizing said alkane hydrocarbon charge at isomerizing conditions including temperature of 300° F.–400° F. and pressure of 100–1000 psig in the presence of isomerization catalyst in the presence of 0.1–5 moles of added hydrogen per mole of hydrocarbon charge, wherein the space velocity (LHSV) of the total charge is 0.5–8;
  b. withdrawing from said isomerization an isomate containing isobutane and n-butane in weight ratio of 1.0–2.0:1;
  c. separating normal pentane from said isomate thereby forming a depentanized isomate;
  d. dehydrogenating said depentanized isomate at 900° F.–1100° F. and 0–1000 psig thereby forming a dehydrogenate containing isobutene, isopentene and normal butane, the weight ratio of isobutene to isopentene being 0.4–0.8:1, and the weight ratio of isobutene to n-butane being 1.0–1.5:1;
  e. reacting said dehydrogenate with at least one water-soluble $C_1$ to $C_6$ alkanol in the presence of etherification catalyst at etherification reaction conditions including temperature of 100° F.–300° F. and 50–750 psig thereby forming reaction mixture containing n-butane together with said tertiary butyl ether of a $C_1$ to $C_6$ alkanol and said tertiary amyl ether of a $C_1$ to $C_6$ alkanol;
  f. contacting said reaction mixture with water thereby forming (i) aqueous extract containing water-soluble alcohol and (ii) raffinate containing said normal butane and said product ethers substantially free of said water-soluble alcohol;

g. recovering said raffinate from said contacting operation; and h. recovering from said raffinate said tertiary butyl ether of a $C_1$ to $C_6$ alkanol and said tertiary amyl ether of a $C_1$ to $C_6$ alkanol.

3. The method of preparing a mixture of a tertiary butyl ether of a $C_1$ to $C_6$ alkanol and a tertiary amyl ether of a $C_1$ to $C_6$ alkanol from a hydrocarbon charge containing normal butane and normal pentane which comprises a. isomerizing said hydrocarbon charge containing normal butane and normal pentane at isomerizing conditions including temperature of 300° F.–400° F. and pressure of 300–700 psig in the presence of isomerization catalyst and in the presence of 0.1–5 moles of added hydrogen per mole of hydrocarbon charge, wherein the space velocity (LHSV) of the total charge is 0.5–8;

b. withdrawing from said isomerization an isomate containing normal butane, normal pentane, isopentane, and isobutane wherein the weight ratio of isobutane to normal butane is 1–2:1;

d. dehydrogenating said depentanized isomate at 900° F.–1100° F. and 0–1000 psig thereby forming a dehydrogenate containing isobutene, isopentenes, normal butane, and being substantially free of normal pentane the weight ratio of isobutene to n-butane being 1–3:1;

e. reacting said dehydrogenate with at least one water-soluble $C_1$ to $C_6$ alkanol in the presence of etherification catalyst at etherification reaction conditions including temperature of 100° F.–300° F. and 50–750 psig thereby forming reaction mixture containing product ethers;

f. contacting said reaction mixture with water in the presence of normal butane, said n-butane being substantially free of normal pentane thereby forming (i) aqueous extract containing water-soluble alcohol and (ii) raffinate containing said normal butane and said product ether substantially free of water-soluble alcohol;

g. recovering said raffinate from said contacting operation; and h. recovering from said raffinate said tertiary butyl ether of a $C_1$ to $C_6$ alkanol and said tertiary amyl ether of a $C_1$ to $C_6$ alkanol.

4. The method of preparing ether from an alkane hydrocarbon charge containing normal butane which comprises a. isomerizing said alkane hydrocarbon charge at isomerizing conditions including temperature of 300° F.–400° F. and pressure of 100–1000 psig in the presence of 0.1–5 moles of added hydrogen per mole of charge hydrocarbon wherein the space velocity LHSV of the total charge is 0.5–8, in the presence of an isomerization catalyst;

b. withdrawing from said isomerization an isomate containing isobutane and n-butane in weight ratio of 1–2:1;

c. dehydrogenating said isomate at 900° F.–1100° F. and 0–1000 psig thereby forming a dehydrogenate containing isobutene and n-butane in weight ratio of 1–3:1;

d. reacting said dehydrogenate with methyl alcohol in the presence of etherification catalyst at etherification reaction conditions including temperature of 100° F–300° F. and 50–750 psig thereby forming reaction mixture containing product methyl, t-butyl ether, methyl alcohol, and n-butane;

e. contacting said reaction mixture with water thereby forming (i) aqueous extract containing methyl alcohol and (ii) raffinate containing said normal butane and said product methyl, t-butyl ether substantially free of said methyl alcohol;

f. recovering said raffinate from said contacting operation; and g. recovering said product methyl t-butyl ether from said raffinate.

5. The method of preparing ether from an alkane hydrocarbon charge containing normal butane which comprises a. isomerizing said alkane hydrocarbon charge at isomerizing conditions including temperature of 300° F.–400° F. and pressure of 100–1000 psig in the presence of 0.1–5 moles of added hydrogen per mole of charge hydrocarbon wherein the space velocity LHSV of the total charge is 0.5–8 in the presence of an isomerization catalyst;

b. withdrawing from said isomerization an isomate containing isobutane and n-butane in weight ratio of 1–2:1;

c. dehydrogenating said isomate at 900° F.–1100° F. and 0–1000 psig thereby forming a dehydrogenate containing isobutane and n-butane in weight ratio of 1–3:1;

d. reacting said dehydrogenate with ethyl alcohol in the presence of etherification catalyst at etherification reaction conditions including temperature of 100° F–300° F. and 50–750 psig thereby forming reaction mixture containing product ethyl, t-butyl ether, ethyl alcohol, and n-butane;

e. contacting said reaction mixture with water thereby forming (1) aqueous extract containing ethyl alcohol and (ii) raffinate containing said normal butane and said product ethyl, t-butyl ether substantially free of said ethyl alcohol;

f. recovering said raffinate from said contacting operation; and g. recovering said product ethyl, t-butyl ether from said raffinate.

6. The method of preparing a mixture of methyl tertiary butyl ether and methyl tertiary amyl ether from an alkane hydrocarbon charge containing normal butane and normal pentane which comprises a. isomerizing said alkane hydrocarbon charge at isomerizing conditions including temperature of 300° F.–400° F. and pressure of 100–1000 psig in the presence of isomerization catalyst in the presence of 0.1–5 moles of added hydrogen per mole of hydrocarbon charge wherein the space velocity LHSV of the total charge is 0.5–8;

b. withdrawing from said isomerization an isomate containing isobutane and n-butane in weight ratio of 1–2:1;

c. separating normal pentane from said isomate thereby forming a depentanized isomate;

d. dehydrogenating said depentanized isomate at 900° F.–1100° F. and 0–1000 psig thereby forming a dehydrogenate containing isobutene, isopentene and normal butane, the weight ratio of isobutene to isopentene being 0.4–0.8:1, and the weight ratio of isobutene to n-butane being 1.0–1.5:1;

e. reacting said dehydrogenate with methyl alcohol in the presence of etherification catalyst at etherification reaction conditions including temperature of 100° F.–300° F. and 50–750 psig thereby forming reaction mixture containing n-butane together with said methyl tertiary butyl ether and said methyl tertiary amyl ether;

f. contacting said reaction mixture with water thereby forming (i) aqueous extract containing methyl alcohol and (ii) raffinate containing said normal butane and said methyl, tertiary butyl ether and methyl, tertiary amyl ether substantially free of said methyl alcohol;

g. recovering said raffinate from said contacting operation; and h. recovering from said raffinate said methyl tertiary butyl ether and said methyl tertiary amyl ether.

7. The method of preparing a mixture of ethyl tertiary butyl ether and ethyl tertiary amyl ether from an alkane hydrocarbon charge containing normal butane and normal pentane which comprises a. isomerizing said alkane hydrocarbon charge at isomerizing conditions including temperature of 300° F.–400° F. and pressure of 100–1000 psig in the presence of isomerization catalyst in the presence of 0.1–5 moles of added hydrogen per mole of hydrocarbon charge wherein the space velocity LHSV of the total charge is 0.5–8;

b. withdrawing from said isomerization an isomate containing isobutane and n-butane in weight ratio of 1–2:1;

c. separating normal pentane from said isomate thereby forming a depentanized isomate;

d. dehydrogenating said depentanized isomate at 900° F.–1100° F. and 0–1000 psig thereby forming a dehydrogenate containing isobutene, isopentene and normal butane, the weight ratio of isobutene to isopentene being 0.4–0.8:1, and the weight ratio of isobutene to n-butane being 1.0–1.5:1;

e. reacting said dehydrogenate with ethyl alcohol in the presence of etherification catalyst at etherification reaction conditions including temperature of 100° F.–300° F. and 50–750 psig thereby forming reaction mixture containing n-butane together with said ethyl tertiary butyl ether and said ethyl tertiary amyl ether;

f. contacting said reaction mixture with water thereby forming (i) aqueous extract containing ethyl alcohol and (ii) raffinate containing said normal butane and said ethyl, tertiary butyl ether and ethyl, tertiary amyl ether substantially fee of said ethyl alcohol;

g. recovering said raffinate from said contacting operation; and h. recovering from said raffinate said ethyl, tertiary butyl ether and said ethyl, tertiary amyl ether.

8. The method of preparing a mixture of methyl tertiary butyl ether and methyl tertiary amyl ether from a hydrocarbon charge containing normal butane and normal pentane which comprises a. isomerizing said hydrocarbon charge containing normal butane and normal pentane at isomerizing conditions including temperature of 300° F.–400° F. and pressure of 300–700 psig in the presence of isomerization catalyst in the presence of 0.1–5 moles of added hydrogen per mole of hydrocarbon charge wherein the space velocity LHSV of the total charge is 0.5–8;

b. withdrawing from said isomerization an isomate containing normal butane, normal pentane, isopentane, and isobutane the weight ratio of isobutane to n-butane being 1–2:1;

c. separating normal pentane from said isomate thereby forming a depentanized isomate;

d. dehydrogenating said depentanized isomate at 900° F.–1100° F. and 0–1000 psig thereby forming a dehydrogenate containing isobutene, isopentene, normal butane, and being substantially free of normal pentane the weight ratio of isobutene to n-butane being 1–3:1;

e. reacting said dehydrogenate with methyl alcohol in the presence of etherification catalyst at etherification reaction conditions including temperature of 100° F.–300° F. and 50–750 psig thereby forming reaction mixture containing product ethers;

f. contacting said reaction mixture with water in the presence of normal butane carbon atoms, said normal butane being substantially free of normal pentane thereby forming (i) aqueous extract containing methyl alcohol and (ii) raffinate containing said normal butane and said methyl tertiary butyl ether and methyl tertiary amyl ether substantially free of methyl alcohol;

g. recovering said raffinate from said contacting operation; and h. recovering from said raffinate said methyl tertiary butyl ether and said ethyl, tertiary amyl ether.

9. The method of preparing a mixture of ethyl tertiary butyl ether and ethyl tertiary amyl ether from a hydrocarbon charge containing normal butane and normal pentane which comprises a. isomerizing said hydrocarbon charge containing normal butane and normal pentane at isomerizing conditions including temperature of 300° F.–400° F. and pressure of 300–700 psig in the presence of isomerization catalyst in the presence of 0.1–5 moles of added hydrogen per mole of hydrocarbon charge wherein the space velocity LHSV of the total charge is 0.5–8;

b. withdrawing from said isomerization an isomate containing normal butane, normal pentane, isopentane, and isobutane the weight ratio of isobutane to n-butane being 1–2:1;

c. separating normal pentane from said isomate thereby forming a depentanized isomate;

d. dehydrogenating said depentanized isomate at 900° F.–1100° F. and 0–1000 psig thereby forming a dehydrogenate containing isobutene, isopentene, normal butane, and being substantially free of normal pentane the weight ratio of isobutene to n-butane being 1–3:1;

e. reacting said dehydrogenate with ethyl alcohol in the presence of etherification catalyst at etherification reaction conditions including temperature of 100° F.–300° F. and 50–750 psig thereby forming reaction mixture containing product ethers;

f. contacting said reaction mixture with water in the presence of normal butane said normal butane being substantially free of normal pentane thereby forming (i) aqueous extract containing ethyl alcohol and (ii) raffinate containing said normal butane and said ethyl tertiary butyl ether and said ethyl tertiary amyl ether substantially free of ethyl alcohol;

g. recovering said raffinate from said contacting operation; and h. recovering from said raffinate said ethyl, tertiary butyl ether and said ethyl, tertiary amyl ether.

* * * * *

UNITED STATES PATENT AND TRADEMARK OFFICE
CERTIFICATE OF CORRECTION

PATENT NO. : 4,118,425
DATED : October 3, 1978
INVENTOR(S) : Sheldon Herbstman

It is certified that error appears in the above-identified patent and that said Letters Patent are hereby corrected as shown below:

Col. 12, line 41, after "catalyst", insert -- and --.

Col. 13, after line 22, insert the following paragraph:

-- c. separating a normal pentane from said isomate thereby forming a depentanized isomate --.

Col. 14, line 20, after "8" insert -- a comma --.

Col. 16, line 49, after "pentane", insert -- a comma --;

Col. 16, line 57, after "butane", insert -- a comma --.

Signed and Sealed this

Fourth Day of December 1979

[SEAL]

Attest:

SIDNEY A. DIAMOND

Attesting Officer  Commissioner of Patents and Trademarks